(12) United States Patent
Ando et al.

(10) Patent No.: US 7,610,820 B2
(45) Date of Patent: Nov. 3, 2009

(54) BIOLOGICAL INFORMATION PRESSURE SENSOR AND BIOLOGICAL INFORMATION PRESSURE DETECTOR

(75) Inventors: Mitsuhiro Ando, Toyohashi (JP); Shunsuke Kogure, Toyota (JP)

(73) Assignee: Aisin Seiki Kabushiki Kaisha, Kariya-shi (JP)

( * ) Notice: Subject to any disclaimer, the term of this patent is extended or adjusted under 35 U.S.C. 154(b) by 353 days.

(21) Appl. No.: 11/560,609

(22) Filed: Nov. 16, 2006

(65) Prior Publication Data

US 2007/0112283 A1    May 17, 2007

(30) Foreign Application Priority Data

Nov. 17, 2005    (JP) .............................. 2005-333291

(51) Int. Cl.
*G01L 1/26* (2006.01)
(52) U.S. Cl. .................................... 73/862.391; 73/777
(58) Field of Classification Search .................. 73/777, 73/862.391
See application file for complete search history.

(56) References Cited

U.S. PATENT DOCUMENTS

| 6,271,760 | B1 * | 8/2001 | Watanabe et al. ............ 340/667 |
| 6,863,136 | B2 * | 3/2005 | Bar-Cohen et al. ............ 175/55 |
| 2006/0016055 | A1 * | 1/2006 | Wilkie et al. ................ 29/25.35 |
| 2006/0150975 | A1 * | 7/2006 | Sullivan ................. 128/204.23 |
| 2006/0207341 | A1 |  9/2006 | Ando et al. |

FOREIGN PATENT DOCUMENTS

JP        2000-230853         8/2000

* cited by examiner

*Primary Examiner*—Max Noori
(74) *Attorney, Agent, or Firm*—Oblon, Spivak, McClelland, Maier & Neustadt, L.L.P.

(57) ABSTRACT

A biological information pressure sensor having a planer shape disposed on an elastic support element for supporting a human body, for detecting an external force due to one or both of a load variation caused by the human body and vibration generated by the human body. The sensor includes a sensing portion having sensitivity with respect to the external force, wherein the sensing portion is configured by using a piezoelectric material, and is configured to have flexibility and anisotropy.

19 Claims, 6 Drawing Sheets

BIOLOGICAL INFORMATION PRESSURE SENSOR AND BIOLOGICAL INFORMATION PRESSURE DETECTOR

CROSS REFERENCE TO RELATED APPLICATIONS

This application is based on and claims priority under 35 U.S.C. §119 with respect to Japanese Patent Application 2005-333291, filed on Nov. 17, 2005, the entire content of which is incorporated herein by reference.

FIELD OF THE INVENTION

This invention generally relates to a pressure sensor for biological information and a pressure detector device for biological information and more particularly to a sheet type (planer type) pressure sensor for biological information which is provided in an elastic support member for supporting human body and which detects external force generated by a load displacement of the human body supported on the support member and by a vibration generated by the human body.

BACKGROUND OF THE INVENTION

Conventionally, various planer type pressure sensors are proposed which detect a load applied on a support member, such as a bed, a mattress or a seat and judge whether a human, an animal or an object exists thereon or not. Some are proposed which detect minute vibration generated by a human heartbeat or breath in addition to the object existence judgment. The following patent document 1 illustrates an invention relating to such load-detecting device. The load detecting device of the patent document 1 includes a vibration detecting means which is provided in a support member supporting a human body and which includes a vibration generating portion and a vibration detecting portion provided adjacent to the vibration generating portion. The load-detecting device of this document includes a vibration characteristic calculation means and a load calculation means. The vibration characteristic calculation means calculates vibration characteristic of the vibration transmitted from the vibration-generating portion based on the output signal from the vibration-detecting portion. The load calculation means calculates the load applied to the vibration detecting means based on the output signal from the vibration characteristic calculation means. Further, the load-detecting device includes a human body extracting means, which extracts vibration component of the supported human body from the output signal from the vibration-detecting portion. This extracting means extracts vibration component such as heartbeat or aspiration (breath).

Patent Document 1 (JP2000-230853A, paragraph 8 to 16, FIG. 1 to 5, 8 to 10)

When a human body is supported by a supporting member a load constantly generated thereby is called a static load and the vibration component of the load extracted from the human body vibration extracting portion based on the heartbeat or aspiration is called as a dynamic load generated suddenly Since the vibration of this dynamic load is very small and the output thereof is not so large. In order to easily detect such small vibration, a piezoelectric element is used as the vibration-detecting portion (see patent document 1 above) to enlarge the sensing area. If such enlargement of the sensing area is performed, some foreign (other than human body) noises may be detected.

A flexible material such as polyurethane material is normally used for the supporting member for supporting human body, considering the comfort issue. When the piezoelectric element is arranged between the supporting member and the human body, the piezoelectric element may be deformed undesirably for detecting the small vibration due to the static load generated by the human body. This deformation may cause output performance of the piezoelectric element or S/N ratio. Particularly, since the heartbeat vibration signal is very small, the output performance and S/N ratio may drop to deteriorate the detection accuracy.

Accordingly, this invention pertains to improve the detection accuracy especially to improve the detection of a load displacement caused by a human body supported on a flexible supporting member or the vibration generated by the human body.

SUMMARY OF THE INVENTION

According to one aspect of the invention, a biological information pressure sensor having a planer shape disposed on an elastic support element for supporting a human body, for detecting an external force due to one or both of a load variation caused by the human body and vibration generated by the human body. The sensor comprises a sensing portion having sensitivity with respect to the external force, wherein the sensing portion is configured by using a piezoelectric material, and is configured to have flexibility and anisotropy by partially varying thickness.

If at least one of the pluralities of the provided sensing portions is easily flexed in a direction different from the other sensing portions, only such one sensing potion has a different sensitivity characteristic. That is, in the case where the other sensing portion has anisotropy such that sensitivity corresponding to a detection purpose is provided, conversely, the sensing portion is capable of detecting an external force applied to a direction that is different from the one in detection purpose. The external force applied to the direction that is different from the one in detection purpose is a noise-based external force. Therefore, detection accuracy is improved by comprehensively utilizing the detection results caused by the sensing portions having different sensitivity directions from each other.

Here, at least one of the sensing portions may be configured to have anisotropy that is orthogonal to the other sensing portions.

If eases of flexing are different from each other in an orthogonal direction, the directions of the external forces, each of which has sensitivity, are the most distant from each other. As a result, in the case where the detection results caused by the sensing portions that are different from each other in sensitivity direction are comprehensively utilized, it is hardly subjected to interference of other external force.

In addition, the biological information pressure detector according to the present invention is equipped with the biological information pressure sensor according to the present invention, and has the following features.

That is, the biological information pressure sensor is disposed at a position at which a load of the human body is applied in the case where the human body is in an ordinary posture. The sensing portions are easily flexed in a direction along a curved face of the human body for elastically deforming the support element in the case of the ordinary posture, and are configured to have anisotropy that is easily flexed in a direction orthogonal to the flexing direction.

The human body and the support element come into closely contact with each other at a position at which the load caused by the human body is applied in the case where the human body is in an ordinary posture. Therefore, if the biological information pressure sensor (sensing portion) is disposed at this position, the biological information pressure sensor is firmly sandwiched between the support element and the human body, and vibration caused by the human body is easily propagated to the biological information pressure sensor. At this time, if sensing portions of the biological information pressure sensor are deformed (flexed) in an isotropic manner in every direction, there is a possibility that a stress is compensated for at the sensor portion.

However, in the present invention, the sensing portions of the biological information pressure sensor is configured to have anisotropy which is easily deformed (flexed) in a direction along a curved face of the human body for elastically deforming the support element in the case where the human body is in ordinary posture and which is hard to be deformed (flexed) in a direction orthogonal to the flexed direction.

Therefore, the compensation for the stress as described above is restrained, and then, load variation or vibration can be detected to have good sensitivity.

In addition, the biological information pressure detector according to the present invention includes a plurality of biological information pressure sensors according to the present invention.

This detector is characterized in that at least one of the biological information pressure sensors is disposed at a position at which the external force caused by the human body is not directly applied in the case where the human body is in an ordinary posture.

If at least one of the plurality of the provided biological information pressure sensors is disposed at a position at which an external force caused by the human body is not directly applied, conversely, the one biological information pressure sensor is provided as a sensor for detecting only an external force that is different from the one in detection purpose. An external force different from the one in detection purpose is a noise-based external force.

Therefore, detection accuracy is improved by comprehensively utilizing the detection results caused by the plurality of biological information pressure sensors.

At this time, all of the biological information pressure sensors including those in which an external force caused by a human body is not applied may have anisotropy that is easily flexed with respect to external forces in the same direction.

That is, there is a high possibility that the external force detected by the biological information pressure sensor in which the external force caused by the human body is not applied may be caused by vibration of a support element itself that is commonly associated with all of the biological information pressure sensors. Therefore, noise content is well restrained at the time of comprehensively utilizing the detection results caused by the plurality of biological information pressure sensors.

BRIEF DESCRIPTION OF THE DRAWINGS

The foregoing and additional features and characteristics of the present invention will become more apparent from the following detailed description considered with reference to the accompanying drawings, wherein.

DETAILED DESCRIPTION OF THE INVENTION

Figure 1A:
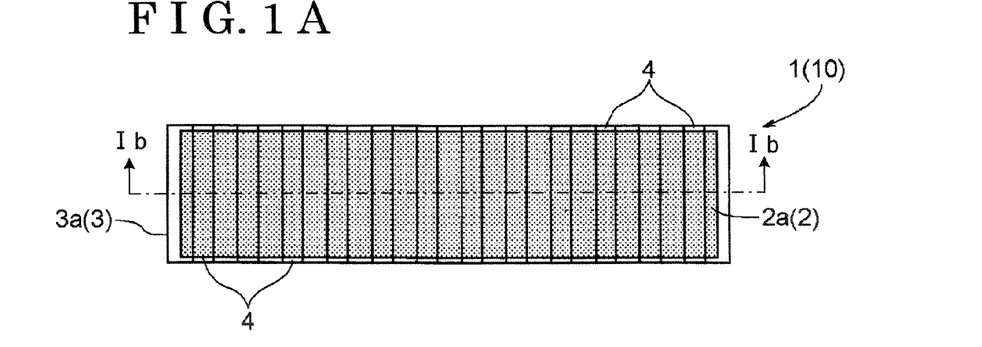
FIG. 1(a) is a schematic diagram of a sensing portion of the biological information pressure sensor according to the invention illustrating a topside view thereof.
Figure 1B:
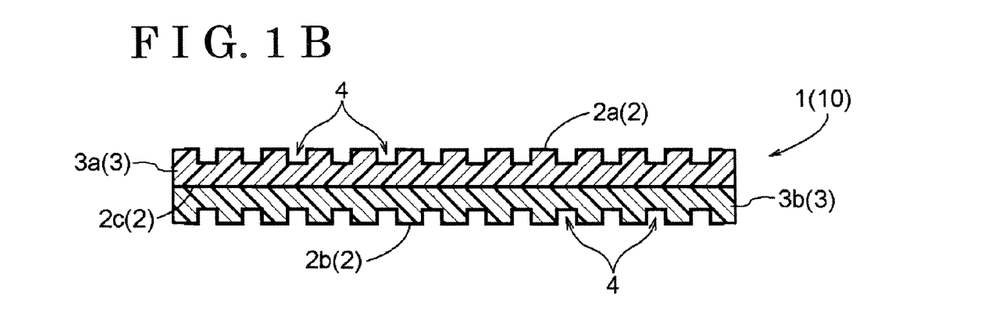
FIG. 1(b) is a schematic diagram of a sensing portion of the biological information pressure sensor according to the invention illustrating a cross sectional view thereof taken along the line 1b-1b of FIG. 1(a)
Figure 2A:
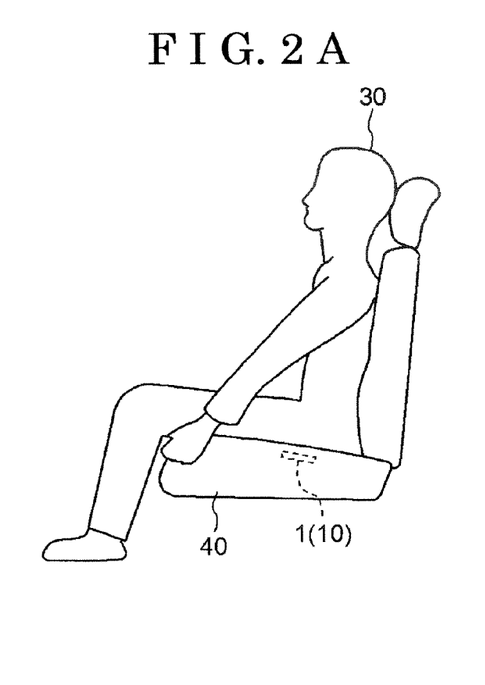
FIG. 2(a) is an explanatory view of arrangement of the biological information pressure sensor on the elastic supporting member illustrating a side view thereof.
Figure 2B:
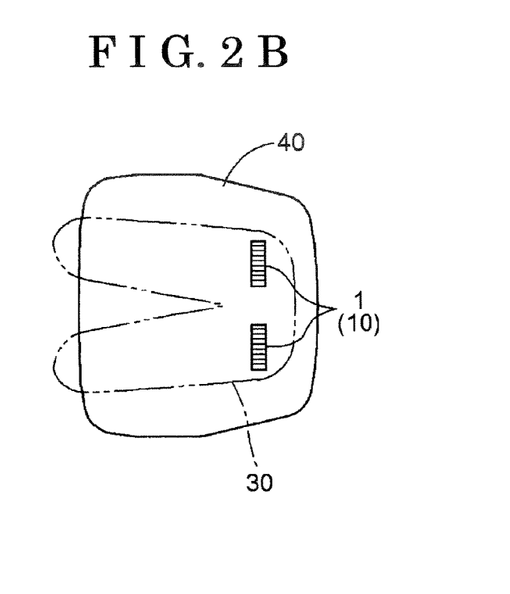
FIG. 2(b) is an explanatory view of arrangement of the biological information pressure sensor on the elastic supporting member illustrating an upper side view thereof.
Figure 3A:
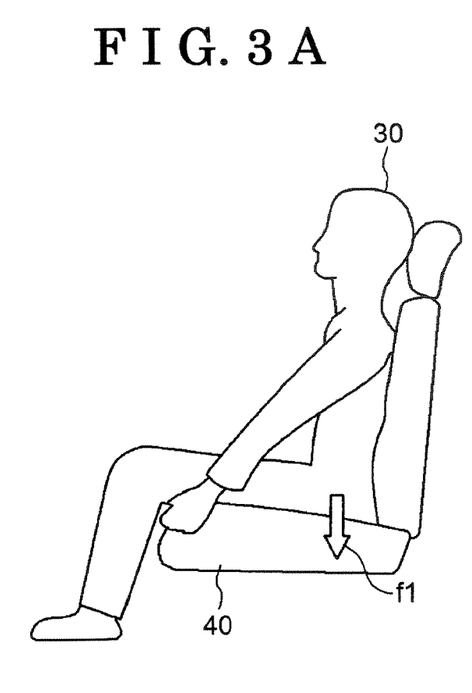
FIG. 3(a) is a view similar FIG. 2(a), but illustrating the human body load applied the elastic supporting member.
Figure 3B:
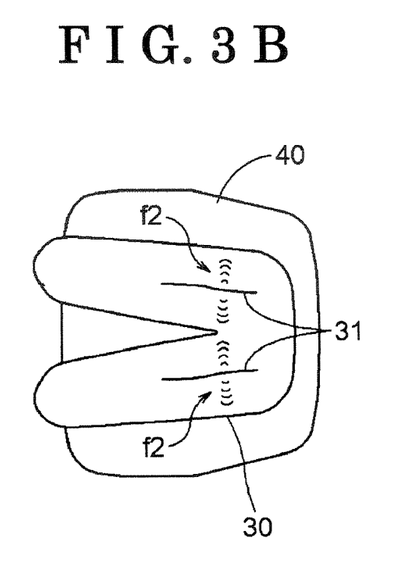
FIG. 3(b) is a view similar to FIG. 2(b), but illustrating a generated vibration from the human body.
Figure 4A:
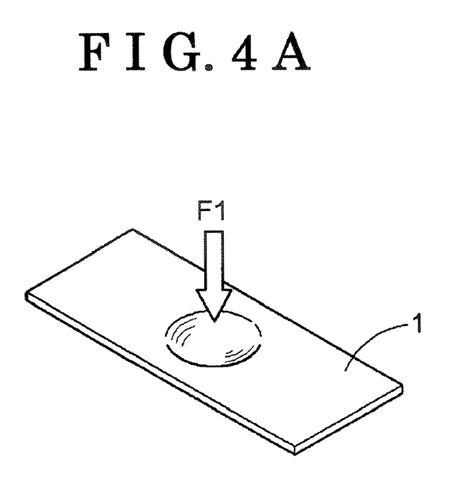
FIG. 4(a) is an explanatory view of anisotropy of the sensing portion.
Figure 4B:
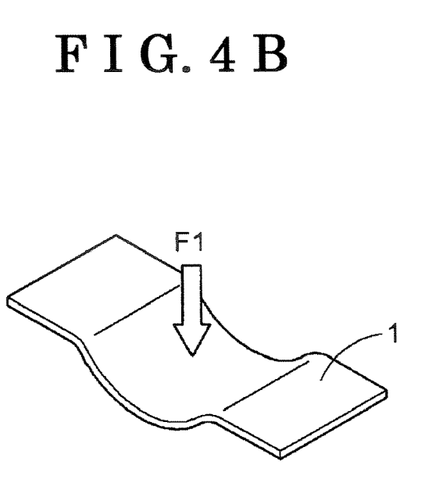
FIG. 4(b) is a view similar to FIG. 3(a), but showing a different shape.

Hereinafter, embodiments of the present invention will now be described with reference to the accompanying drawings. FIG. 1(a) and FIG. 1(b) are the views schematically depicting a configuration of sensing portions of a planar biological information pressure sensor according to the present invention, FIG. 1(a) is a top view and FIG. 1(b) is a sectional view taken along the line 1b-1b of FIG. 1(a). FIG. 2(a) and FIG. 2(b) are the illustrative views illustrating an example of disposing the biological information pressure sensor on a seat as an elastic support element FIG. 3(a) and FIG. 3(b) are the illustrative views illustrating an example of a load of a human body and vibration generated by the human body in FIG. 2(a) and FIG. 2(b). FIG. 4(a) and FIG. 4(b) are the illustrative views illustrating anisotropy of the ease of flexibility of the sensing portions. For the purpose of convenience, the biological information pressure sensor will be referred to as just "a pressure sensor".

As shown in FIG. 1, a planar sensing portion 1 (pressure sensor 10) comprising a laminated two-layered piezoelectric element (piezoelectric film) having a first piezoelectric element 3a and a second piezoelectric element 3b. The piezoelectric elements are configured by using a piezoelectric material such as poly-vinylidene fluoride (PVDF), and then, an electric charge is generated by electric polarization caused by piezoelectric effect. When an electrode is mounted on the piezoelectric element, the generated electric charge is removed as a voltage signal.

Two electrodes are mounted on one piezoelectric element 3 (3a and 3b), and the piezoelectric element 3 is configured to be sandwiched between these two electrodes. Specifically, as shown in FIG. 1, the first piezoelectric element 3a is sandwiched between a first electrode 2a and an intermediate electrode 2c, and the second piezoelectric element 3b is sandwiched between a second piezoelectric element 2b and the intermediate electrode 2c. That is, with the intermediate electrode 2c being a common electrode, the two-layered piezoelectric elements 3 are laminated to have electrodes that are independent from each other.

In addition, a sensing portion 1 has a groove 4 that is provided when the piezoelectric elements 3 are fabricated. A resin material such as polyvinylidene fluoride that is a material for the piezoelectric element is easily processed in a variety of shapes. Therefore, as shown in FIG. 1, the piezoelectric elements 3 having the groove 4 are formed while thickness of the piezoelectric material is partially varied.

Since the sensing portion 1 has this groove 4, the sensing portion is easily deformed in the longitudinal direction as shown. That is, the sensing portion 1 having flexibility is configured to have anisotropy with respect to the ease of flexing. For example, as shown in FIG. 4 (*a*), in the case where an external force F1 has been applied to the sensing portion 1 which does not have anisotropy (which has isotropy), the sensing portion 1 is deformed in a concentric shape. That is, a stress is also generated in an isotropic manner. However, as shown in FIG. 4 (*b*), in the case where the sensing portion 1 has anisotropy, this sensing portion is deformed in a longitudinal direction with respect to a similar external force F1. That is, the stress is also generated intensively in a predetermined direction.

Hereinafter an embodiment of configuring a biological information pressure detector equipped with this pressure sensor 10 (sensing portion 1) will now be described with respect to a case in which a human body 30 is seated on a seat 40 as an elastic support element.

As shown in FIGS. 2(*a*), 2(*b*) and FIGS. 3(*a*) and 3(*b*), in the case where the human body 30 is in an ordinary posture (normal driving or seating condition), a pressure sensor 10 is disposed at a position at which a load F1 of the human body 30 is applied. At the position at which the load F1 caused by the human body 30 is applied, the human body 30 and the support element 40 come into closely contact with each other. Therefore, when the pressure sensor 10 (sensing portion 1) is disposed at this position, the pressure sensor 10 is firmly sandwiched between the support element 40 and the human body 30, and the vibration caused by the human body 30 is easily propagated to the pressure sensor 10.

At this time, if the sensing portions 1 of the pressure sensor 10 are deformed in an isotropic manner in every direction, there is a possibility that the stress at the sensing portion 1 is compensated for. However, in the present invention, the sensing portion 1 is configured to have anisotropy that is easily flexed in a direction along a curved face of a hip part (or femoral part) of the human body 30 for elastically deforming the support element 40 in the case where the human body 30 is in an ordinary posture and that is hard to be flexed in a direction orthogonal to the flexing direction. Therefore, the compensation of the stress as described above is restrained, and load variation or vibration is detected with good sensitivity.

Further, for example, as shown in FIG. 3 (*b*), blood vessels 31 pass through a dorsal side of the femoral part of the human body 30, and then, the vibration such as pulsation generated by the human body 30 is propagated via the blood vessels 31. As described above, the rigidity of the pressure sensor 10 is high and the pressure sensor 10 is hard to be flexed with respect to the direction along the blood vessels 31. Therefore, even if a timing of pulsation f2 is lagged depending on a site of the blood vessels 31, and then, a lag occurs with an amplitude of the external force applied to the pressure sensor 10, a possibility that a stress is compensated for is restrained. Therefore, the biological information pressure sensor capable of well detecting fine vibration such as pulsation is provided.

Although not shown, a similar concept can be employed in a case of detecting vibration such as respiration by disposing the pressure sensor 10 on a backrest.

As described above, the pressure sensor 10 (sensing portion 1) having anisotropy is properly disposed, thereby making it possible to well detecting fine vibration such as pulsation or respiration generated by the human body. In the present invention, a configuration for further improving detection sensitivity can be employed.

As described above with reference to FIGS. 1(*a*) and 1(*b*), the sensing portions 1 are configured by laminating two-layered piezoelectric elements 3 each having different polarities. In this context, the first piezoelectic element 3a and the second piezoelectric element 3b are configured to have different polarities from each other. This polarity depends on an orientation of the piezoelectric element. The orientation of this alignment, a so-called orientation of piezoelectric activity is achieved in accordance with processing called a polling processing or polarizing processing. In the case where the polarities of the two-layered piezoelectric element 3 are reversed from each other, it becomes possible to obtain a larger output in the case where deformation occurs with respect to the same external force.

Figure 5A:
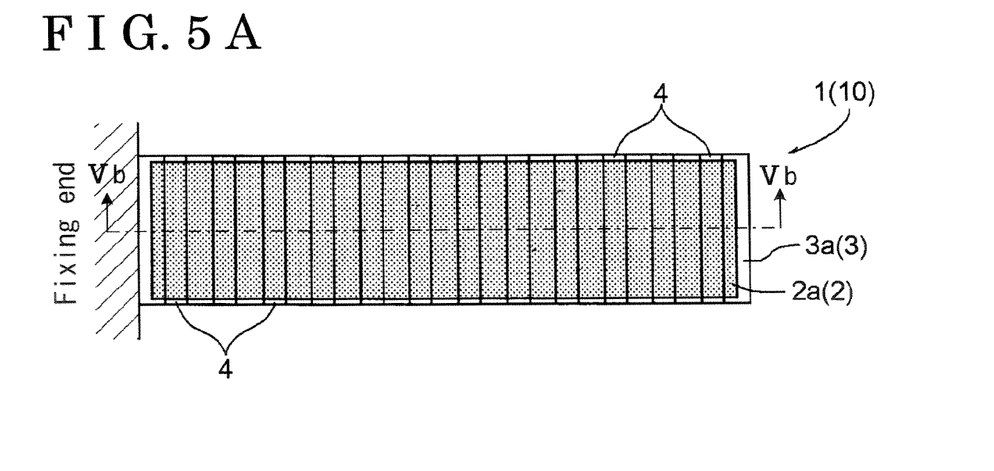
FIG. 5(a) is an explanatory view showing an exterior force being applied on the sensing portion of FIG. 1(a)
Figure 5B:
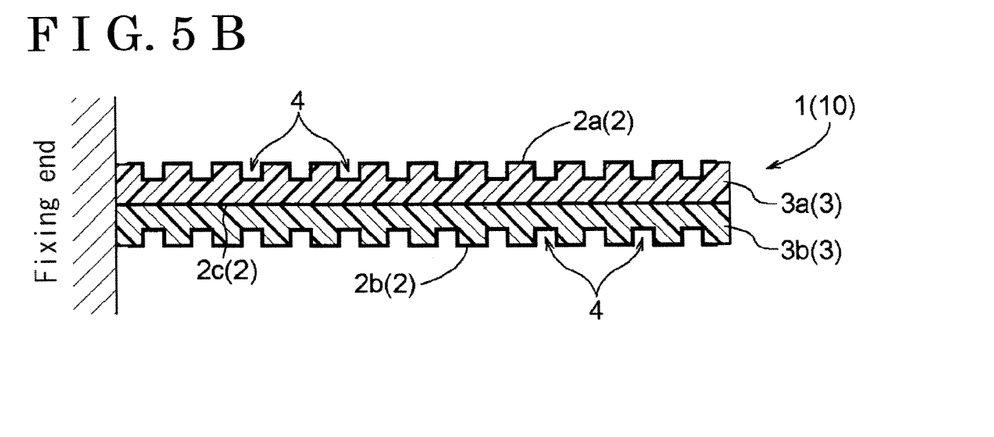
FIG. 5(b) is across sectional explanatory view showing an exterior force being applied on the sensing portion of FIG. 1(b) taken along the line 5b-5b of FIG. 5(a)
Figure 5C:
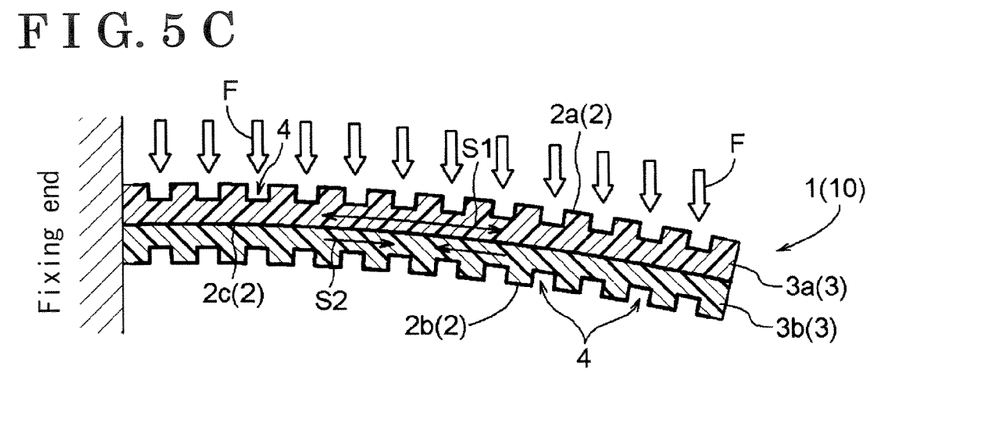
FIG. 5(c) is a view similar to FIG. 5(b), but showing the deformation condition by the external force applied thereon.

This principle will now be described with reference to FIGS. 5(*a*) to 5(*c*). As shown in FIGS. 5(*a*), 5(*b*) and 5(*c*), one end of the longitudinal side of sensing portions 1 shown in FIG. 1(*a*) is fixed to a fixing end, and an external force F is applied vertically from the side of the first piezoelectric element 3a. The sensing portion 1 is deformed in a direction of the external force F. At this time, a tensile stress S1 is produced at the first piezoelectric element 3a in response to the external force F, and a compression stress S2 is produced at the second piezoelectric element 3b. That is, the stresses in their reverse direction are generated at the two-layered piezoelectric element 3 around a center electrode 2c that is a junction portion of these two layers.

Here, the first piezoelectric element 3a and the second piezoelectric element 3b have reverse orientations from each other, and thus, voltage signals having the same polarities are produced on their respective electrodes 2a and 2b with the center electrode 2c as a reference. As a result an output of the sensing portion 1 has amplitude that is twice as wide as each piezoelectric element 3.

As described above, if the plurality of sensing portions 1 having improved detection accuracy and detection sensitivity are provided, the detection range is broadened while the detection accuracy is maintained. That is, the individual sensing portions 1 detect a load variation or vibration, respectively. Thus, even if the detection range is broadened, a possibility that the individual sensing portions 1 are influenced by noise-based vibration is equal to that when the detection range is narrow. In addition, a system making comprehensive judgment is constructed by using the external forces detected by the other sensing portions 1 from each other.

Figures 6A, 6B:
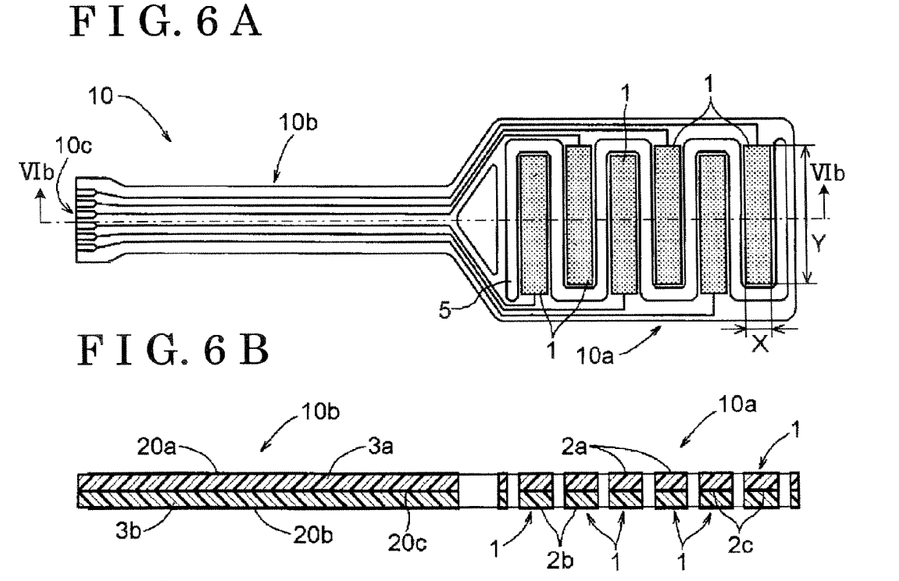
FIG. 6(a) is a view similar to FIG. 1(a), but showing a plurality of sensing portions being arranged.
FIG. 6(b) is a cross sectional view taken along the line 6b-6b of FIG. 6(a)

FIGS. 6(a) and 6(b) each shows a block diagram depicting an example of a pressure sensor 10 equipped with a detector portion 10a comprising a plurality of sensing portions 1 and a wiring portion 10b for transmitting output signals of the plurality of sensing portions 1. Like FIG. 1(a), FIG. 6(a) is a top view and FIG. 6(b) is a sectional view taken along the line 6b-6b of FIG. 6(a).

In the present embodiment, the detector portion 10a is configured to have six sensing portions 1. A slit 5 is provided at the periphery of the sensing portions 1 so as not to influence each other caused by deformations of the sensing portions 1.

The detector portion 10a and the wiring portion 10b are integrally formed with the same material, i.e., the piezoelectric element. A wire 20a from the first electrode 2a of the respective one of the sensing portions 1 pass through the same face as that of the first electrode 2a, and arrives at a terminal portion 10c. That is, the wire 20 passes through a top face side shown in FIG. 6 (b). Similarly, a wire 20b from the second electrode 2b passes through a bottom face side shown in FIG. 6 (b), and then, a wire 20c from the center electrode 2c passes through a center portion that is a junction portion between the first piezoelectric element 3a and the second piezoelectric element 3b, and then, arrives at the terminal portion 10c.

Figures 7A, 7B:
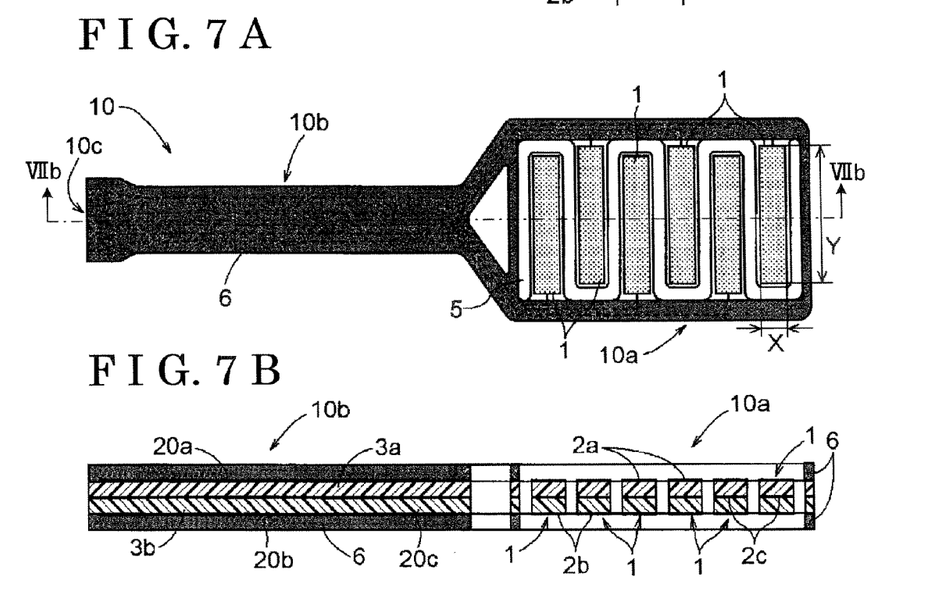
FIG. 7(a) is a view similar to FIG. 6(a), but showing a different embodiment thereof.
FIG. 7(b) is a cross sectional view taken along the line 7b-7b of FIG. 7(a)

FIG. 7(a) and FIG. 7(b) show a further modification of the pressure sensor 10 shown in FIG. 6(a) and FIG. 6(b). As described above, the detector portion 10a and the wring portion 10b are integrally formed with the piezoelectric element, and thus, the wiring portion 10b also has sensitivity relevant to load variation or vibration. Thus, if a stress is generated with respect to an external force applied to the wiring portion 10b, it may have possibilities that the detection results at the detector portion 10a is compensated for and that a signal produced as a noise content is outputted. These possibilities become factors of deteriorating the detection accuracy of the pressure sensor. Therefore, a protective layer 6 is integrally formed at a portion other than that needed to function as a sensing portion 1, in particular, at an outer periphery of the detector portion 10a and the wiring portion 10b. By providing the protective layer 6, the rigidities of these portions is improved and flexibility relevant to the sensing portion 1 of the detector portion 10a is restrained. As a result, at such unnecessary portions, the generation of an electric charge due to a piezoelectric effect is restrained.

As described above, the sensing portion 1 is comprised to have anisotropy in rigidity by providing a groove 4 or the like. In addition, it is preferable that the sensing portion 1 is sandwiched between the support element 40 and a human body 30, and then, is deformed along a curved face of the human body 30. In particular, in a pressure sensor 10 having the plurality of sensing portions 1 as well has been clarified by testing carried out by the inventor, et al that satisfying this deformation is preferable in view of a dimensional aspect ratio of the sensing portion 1 (Y/X of FIG. 6 and FIG. 7).

Figure 8:
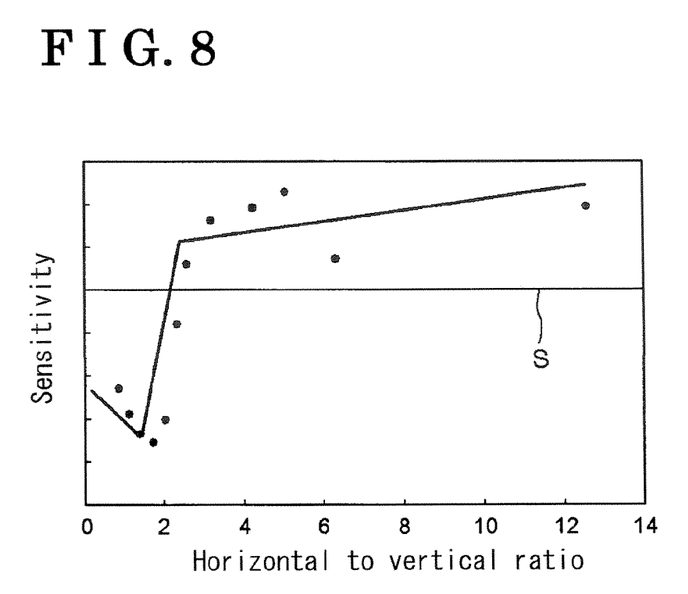
FIG. 8 is a graph showing a relationship between the horizontal to vertical size ratio of the sensing portion and the sensitivity result.

FIG. 8 is a graph of test results showing a relationship between a dimensional aspect ratio and sensitivity of an element (sensing portion 1). Uppercase letter "S" in the graph denotes target sensitivity (for example, output voltage). The Inventor et al investigated a relationship between a dimensional aspect ratio and sensitivity of the sensing portion 1 in the pressure sensor 10 as shown in FIGS. 6(a) and 6(b) and FIGS. 7(a) and 7(b). As a result, in the case where the dimensional aspect ratio is equal to or greater than 3, it has been identified that the target sensitivity is exceeded.

Figure 9A:
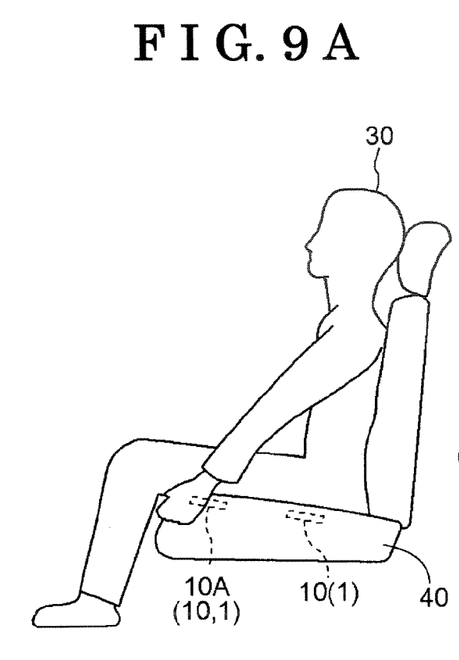
FIG. 9(a) is a view similar to FIG. 2(a), but showing a different embodiment.
Figure 9B:
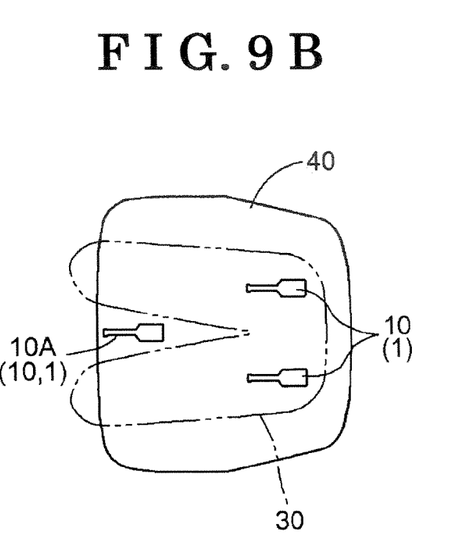
FIG. 9(b) is a view similar to FIG. 2(b), but showing the embodiment of FIG. 9(a)

FIG. 9(a) shows an example of disposing the pressure sensor 10 shown in FIG. 6(a) or FIG. 7(a) on a seat 40 as a support element. As shown in the figure, at least one pressure sensor 10A is disposed at a position at which an external force caused by a human body 30 (load f1 or pulsation f2 shown in FIG. 3(a) or FIG. 3(b)) is not directly applied in the case where the human body 30 is in an ordinary posture.

Conversely, the pressure sensor 10A disposed at the position at which the external force caused by the human body 30 is not directly applied detects only an external force different from the one in detection purpose. The external force different from the one in detection purpose is a noise-based external force. Therefore, detection accuracy is improved by comprehensively utilizing the detection results caused by the plurality of pressure sensors 10.

At this time, it is preferable that all of the pressure sensors including the pressure sensor 10A in which the external force caused by the human body 20 is not applied have anisotropy in rigidity with respect to the external forces in the same direction. That is, there is a high possibility that the external force detected by the pressure sensor 10A in which the external force caused by the human body 30 is not applied is caused by vibration of the seat 40 itself commonly associated with all of the pressure sensors 10. Therefore, noise content is well restrained at the time of comprehensively utilizing the detection results caused by the plurality of pressure sensors 10.

Figure 10:
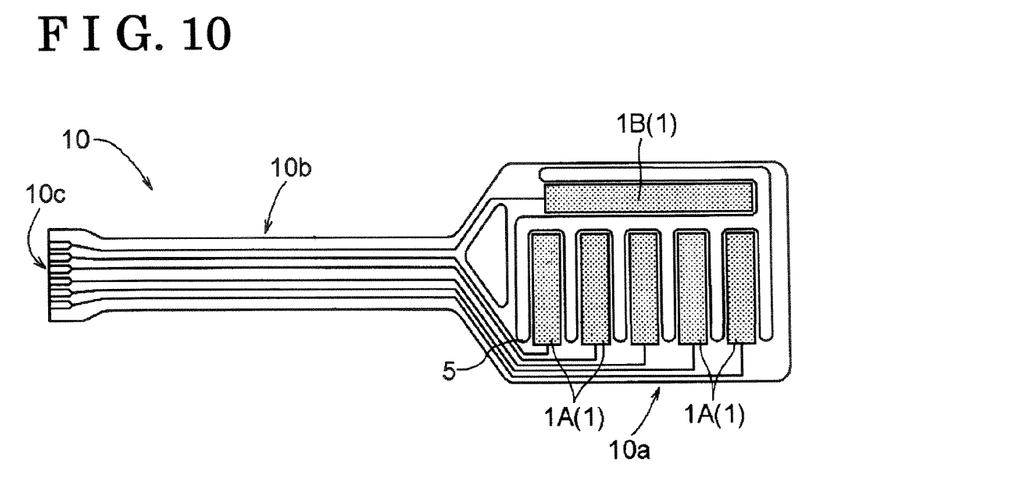
FIG. 10 is a view similar to FIG. 6(a), but showing another embodiment.

In addition, as shown in FIG. 10, a pressure sensor 10 equipped with the plurality of sensing portions 1 may be configured so that at least one sensing portion 1B has anisotropy that is different from the other sensing portion 1A.

With such a configuration, only one sensing portion 1B has a different sensitivity characteristic from other sensing portions. That is, in the case where the sensing portion 1A other than such one sensing portion has anisotropy such that the sensitivity corresponding to a detection purpose is provided, conversely, the sensing portion 1B is provided as a sensing portion 1 capable of detecting an external force applied in a direction different from the one in detection purpose. The external force applied in a direction different from the one in detection portion is a noise-based external force. Therefore, detection sensitivity can be improved by comprehensively utilizing the detection results caused by the sensing portion 1A and the sensing portion 1B that are different from each other in sensitivity direction.

At this time, at least one sensing portion 1 (for example, sensing portion 1B) may have anisotropy orthogonal to the other sensing portion 1A. If the eases of flexing are different from each other in orthogonal direction, the directions of the external forces having sensitivities each other become the most distant. As a result, interference of other external force is hardly received in the case of comprehensively utilizing the detection results by the sensing portions that are different from each other in sensitivity direction.

The configuration described above is favorable at the aspect of restraining influence such as vibrations due to the support element itself caused by the noise-based external force whose sensing portions 1 (1A and 1B) have sensitivity.

For example, as shown in FIGS. 3(a) and 3(b), in the case where the vibration generated by the human body 30 such as pulsation is detected via the blood vessels 31 passing through the dorsal side of the femoral part of the human body 30, the sensing portion 1A and the sensing portion 1B are used as a pulsation (heart rate) detection sensor and a reference sensor, respectively. The reference sensors (sensing portions 1B) are disposed adjacently in orthogonal manner to the pulsation detection sensors (sensing portions 1A), whereby the same noise content due to the vibration of the support element 40 itself is included as described above, in outputs of the pulsation detection sensor and the reference sensor. However, a signal caused by pulsation is not included in the output from the reference sensor or becomes small if it is included. Therefore, noise content is eliminated by combining both of them, making it possible to accurately extract a pulsation signal. As a result, a fine vibration such as pulsation or the like is well detected.

For example, in the case where the support element 40 is a vehicle seat and detects pulsation or the like of passengers in the vehicle, the support element 40 itself vibrates due to vibration of the vehicle during driving. In such an environment as well, a fine vibration such as pulsation caused by a human body is well detected.

The pressure sensor 10 having the plurality of sensing portions 1 may be disposed at a position as shown in FIG. 2(a), and conversely, the pressure sensor 10 having a single sensing portion 1 may be disposed as shown in FIG. 9(a).

In addition, in the foregoing description, there has been employed a configuration in which two-layered piezoelectric elements 3a and 3b are laminated on a sensing portion 1, as shown in FIG. 1(a) or 1(b). However, without being limited thereto, for example, as shown in FIG. 11, a sensing portion 1C may be configured while a single-layered piezoelectric element 3 is equipped with electrodes 2a and 2b.

Figure 11:
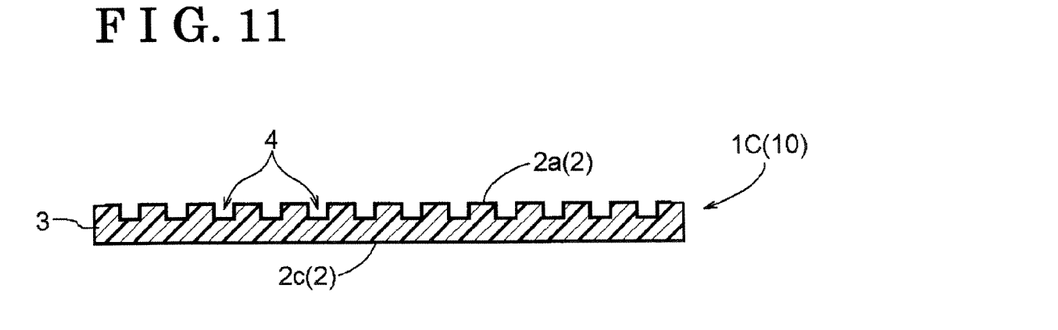
FIG. 11 is a view similar to FIG. 6(b), but showing another embodiment.
Figure 12:
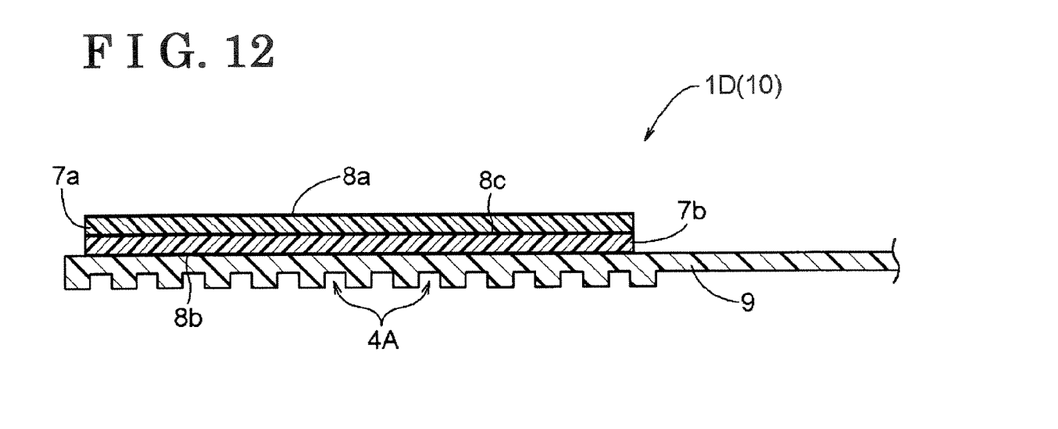
FIG. 12 is a view similar to FIG. 7(b), but showing another embodiment.

Further, while the sensing portion 1 has been integrally formed using the same piezoelectric material in the examples shown in FIG. 1(a) and FIG. 11, a structure as shown in FIG. 12 may be employed. In other words, a groove 4A is provided at a substrate 9 (base portion) for holding piezoelectric elements 7a and 7b that are sensitive portions, and then, thickness of the substrate 9 is partially varied. Then, a sensing portion 1D is configured to have the substrate 9, the piezoelectric elements 7a and 7b, and electrodes 8a, 8b, and 8c.

The piezoelectric element, of course, may be configured to have a single layer without being limited to the two layers. In addition, although not shown, a piezoelectric element 3 is flatly formed at the sensing portion shown in FIG. 1(a) or FIG. 11, and an electrode 2 (for example, the first electrode 2a and the second electrode 2b) is formed in a waved shape, whereby irregularities may be formed at a cross section. In this manner, a wave-formed electrode is equivalent to a base portion according to the present invention.

As described above, according to the present invention, there can be provided a biological information pressure sensor and a biological information pressure detector, being capable of accurately detecting a load variation caused by a human body supported by the elastic support element or a vibration caused by the human body.

While the foregoing embodiments have illustrated a case of detecting pulsation of a human body sitting on a seat, the applicable scope of the present invention is not limited thereto. The present invention can be applied in order to detect a fine vibration such as pulsation or respiration or a motion of a human body due to a load variation on a bed or a wheel chair, or a toilet with a bidet function.

What is claimed is:

1. A biological information pressure sensor having a planer shape disposed on an elastic support element that supports a human body, wherein the sensor detects an external force due to one or both of a load variation caused by the human body and vibration generated by the human body, the sensor comprising:
a sensing portion that detects the vibration generated by the human body, wherein the sensing portion includes a piezoelectric material that includes a plurality of different thicknesses so as to be more flexible in a predetermined direction of the sensing portion than in other directions of the sensing portion.

2. The biological information pressure sensor according to claim 1, wherein the sensor includes a plurality of the sensing portions, and wherein a detecting portion having the plurality of sensing portions and a wiring portion that transmits output signals of the plurality of the sensing portions are formed using an identical material, and wherein the wiring portion is configured to be harder than the detecting portion.

3. The biological information pressure sensor according to claim 1, wherein the sensor includes a plurality of the sensing portions, and at least one of the sensing portions has anisotropy that is different from the other sensing portions.

4. The biological information pressure sensor according to claim 3, wherein at least one of the sensing portions has anisotropy that is orthogonal to the other sensing portions.

5. The biological information pressure sensor according to claim 2, wherein the plurality of sensing portions are arranged through slit means.

6. The biological information pressure sensor according to claim 1, wherein a groove is provided on an outer surface of the sensing portion so that the thickness of the piezoelectric material is partially varied.

7. A biological information pressure detector having the biological information pressure sensor according to claim 1, wherein the biological information pressure sensor is disposed at a position at which a load of the human body is applied in the case where the human body is in an ordinary posture, and wherein the sensing portion is configured to have anisotropy that is easily flexed in a direction along a curved surface of the human body for elastically deforming the support element in the case of the ordinary posture and that is hard to flex in a direction orthogonal to the flexing direction.

8. A biological information pressure detector having a plurality of the biological information pressure sensors according to claim 1, wherein at least one of the biological information pressure sensors is disposed at a position at which the external force caused by the human body is not directly applied in the case where the human body is in an ordinary posture.

9. The biological information pressure sensor according to claim 1, wherein the plurality of different thicknesses are arranged in an alternating pattern formed by at least one groove.

10. The biological information pressure sensor according to claim 1, wherein the plurality of different thicknesses include an alternating arrangement of thin portions and thick portions.

11. A biological information pressure sensor having a planer shape disposed on an elastic support element that supports a human body, wherein the sensor detects an external force due to one or both of a load variation caused by the human body and vibration generated by the human body, the sensor comprising:
a sensing portion having sensitivity with respect to the external force, wherein the sensing portion includes a piezoelectric material, and is configured to have flexibility and anisotropy,
wherein a groove is provided on an outer surface of the sensing portion so that the thickness of the piezoelectric material is partially varied.

12. A biological information pressure sensor having a planer shape disposed on an elastic support element that supports a human body, wherein the sensor detects an external force due to one or both of a load variation caused by the human body and vibration generated by the human body, the sensor comprising:

a sensing portion that detects the vibration generated by the human body, wherein the sensing portion includes a sensor portion formed by a piezoelectric material and a base portion that holds the sensor portion, the base portion including a plurality of different thicknesses so as to be more flexible in a predetermined direction of the sensing portion than in other directions of the sensing portion.

13. The biological information pressure sensor according to claim 12, wherein the sensor includes a plurality of the sensing portions, and at least one of the sensing portions has anisotropy that is different from the other sensing portions.

14. The biological information pressure sensor according to claim 13, wherein at least one of the sensing portions has anisotropy that is orthogonal to the other sensing portions.

15. The biological information pressure sensor according to claim 12, wherein the plurality of sensing portions are arranged through slit means.

16. A biological information pressure detector having the biological information pressure sensor according to claim 12, wherein the biological information pressure sensor is disposed at a position at which a load of the human body is applied in the case where the human body is in an ordinary posture, and wherein the sensing portion is configured to have anisotropy that is easily flexed in a direction along a curved surface of the human body for elastically deforming the support element in the case of the ordinary posture and that is hard to flex in a direction orthogonal to the flexing direction.

17. A biological information pressure detector having a plurality of the biological information pressure sensors according to claim 12, wherein at least one of the biological information pressure sensors is disposed at a position at which the external force caused by the human body is not directly applied in the case where the human body is in an ordinary posture.

18. The biological information pressure sensor according to claim 12, wherein the plurality of different thicknesses are arranged in an alternating pattern formed by at least one groove.

19. The biological information pressure sensor according to claim 12, wherein the plurality of different thicknesses include an alternating arrangement of thin portions and thick portions.

* * * * *